United States Patent
Namiki et al.

[11] Patent Number: 5,977,310
[45] Date of Patent: Nov. 2, 1999

[54] PEG-MODIFIED HGF

[75] Inventors: Mitsuo Namiki, Takarazuka, Japan; Naoto Kusunose, San Diego, Calif.; Noriko Akimaru, Nishinomiya, Japan

[73] Assignee: Toshikazu Nakamura and Sumitomo Pharmaceuticals Co., Ltd., Osaka, Japan

[21] Appl. No.: 08/913,236

[22] PCT Filed: Mar. 7, 1996

[86] PCT No.: PCT/JP96/00599

§ 371 Date: Nov. 4, 1997

§ 102(e) Date: Nov. 4, 1997

[87] PCT Pub. No.: WO96/28475

PCT Pub. Date: Sep. 19, 1996

[30] Foreign Application Priority Data

Mar. 10, 1995 [JP] Japan ........................ 7-79669

[51] Int. Cl.⁶ .......................... A61K 38/18; A61K 38/19; C07K 1/113; C07K 14/475
[52] U.S. Cl. .......................... 530/351; 424/85.1; 514/21; 530/399; 530/410
[58] Field of Search .................. 424/85.1; 519/8, 519/12, 21; 530/350, 395, 397, 399, 410, 351

[56] References Cited

U.S. PATENT DOCUMENTS

| | | | |
|---|---|---|---|
| 5,316,921 | 5/1994 | Godowski et al. | 435/69.4 |
| 5,324,844 | 6/1994 | Zalipsky | 548/520 |
| 5,654,404 | 8/1997 | Roos et al. | 530/387.3 |

FOREIGN PATENT DOCUMENTS

| | | |
|---|---|---|
| 61-249388 | 11/1986 | Japan . |
| 3-95200 | 4/1991 | Japan . |
| 4-108827 | 4/1992 | Japan . |
| 94/20069 | 9/1994 | WIPO . |
| 94/23740 | 10/1994 | WIPO . |

*Primary Examiner*—Jeffrey E. Russel
*Attorney, Agent, or Firm*—Birch, Stewart, Kolasch & Birch, LLP

[57] ABSTRACT

This invention relates to a PEG-modified HGF (Hepatocyte Growth Factor), namely HGF modified by polyethylene glycol. The PEG-modified HGF of the invention has a prolonged clearance in vivo, effectively exhibits its physiological activity for a long period of time, and has the same physiological activity as HGF, which makes it possible to reduce the dose and relieve the side effects of the same.

2 Claims, 3 Drawing Sheets

PEG-MODIFIED HGF

FIELD OF THE INVENTION

This invention relates to a PEG-modified HGF, namely Hepatocyte Growth Factor (HGF) modified by an agent comprising a Polyethylene Glycol (PEG) moiety. This invention also relates to a pharmaceutical composition comprising administering to a patient an effective amount of PEG-modified HGF, for treating hepatic diseases, treating renal diseases, promoting growth of epithelial cells, treating cancer, reducing side effects of anti-cancer reagents, treating lung diseases, treating gastric and duodenal diseases, treating cerebral and nerval injury, increasing platelets, treating hypoptoteinemia, healing wounds, increasing hemopoietic stem cells, restoring hair, as a component of skin cosmetics.

BACKGROUND OF THE INVENTION

HGF is a unique cytokine having various activities not limited to controlling growth of hepatocytes, and growth of various epithelium cells, but also extended to enhancing motility of cells, and inducing morphogenesis with constructing three dimensional tissue. HGF takes a main role in generation or regeneration of tissues and organs as a mitogen, a motogen and a morphogen.

HGF is a heterodimeric protein comprising an α chain having a molecular weight of about 69 kD and a β chain having a molecular weight of about 34 kD, and having a molecular weight 82–85 kD as a whole.

HGF acts as a growth factor for promoting growth of not only hepatocytes, but also renal tubule epithelial cells, keratinocytes, melanocytes, alveolar epithelial cells type II, gastric mucosal epithelial cells, vascular endthelial cells, and other epithelial cells.

HGF shows an activity for promoting growth of normal cells, but shows an activity for suppressing the proliferation of tumor cells (Tajima, H. et al., FEBS Lett., 291, 229, 1991).

HGF also shows an activity for enhancing motility of various epithelial cells such as MDCK cells (normal epithelial cells of renal tubule) and a motogen activity such as scattering colony of cultured said cells.

HGF is reported to have an activity of inducing morphogenesis of MDCK cells (Montesano, R. et al., Cell, 67, 901, 1991).

HGF inhibits leakage of a soluble enzyme from cultured hepatocytes prepared from an animal treated by carbon tetrachloride, a typical toxic substance to liver. These results show that HGF has an anti-hepatitis activity in vitro. HGF is also reported to have an anti-hepatitis activity in vivo (Takehara, T. et al., Biomed. Res., 12, 335, 1991).

HGF is also reported to enhance the activity of Na-K-ATPase in renal tubule epithelial cells and has been suggested to enhance renal functions (Ishibashi, T et al., Biochem. Biophys. Res. Commun., 182, 960, 1992).

Problems in administering HGF in vivo are fast clearance in vivo and that HGF originating from non-human species may have an antigenicity.

One of the effective ways to solve the problems is modifying the protein with a PEG reagent to delay the clearance and to reduce the antigenicity (Yoshimoto, T. et al., Jpn. J. Cancer Res., 77, 1264, 1986; Japanese patent application KOKAI 56-23587, 1981; Japanese patent application KOKAI 61-178926, 1986; Abuchowski, A. et al., Cancer Biochem. Biophys., 7, 175, 1984; Japanese patent application KOKAI 62-115280, 1987).

As described above, HGF has various biological activities and development of HGF derivatives as pharmaceutical agents is expected. It is considered important to develop a pharmaceutical composition for use in a method of treatment, comprising administration to a patient an effective amount of HGF for treating hepatic diseases, treating renal diseases, promoting growth epithelial cells, treating cancer, reducing side effects of anti-cancer reagents, treating lung diseases, treating gastric and duodenal diseases, treating cerebral and nerval injury, increasing platelets, treating hypoptoteinemia, healing wounds, increasing hemopoietic stem cells, restoring hair, and in skin cosmetics, but it is necessary to administer several ten µg/kg to several mg/kg of HGF to have enough activities, and the administration amount may be relatively higher than other physiologically active protein. High dose may be disadvantageous because of unexpected side effects and high cost to manufacture a pharmaceutical product.

The most important problem to be solved is to improve the clearance in vivo, since it is reported that half life time of HGF in blood is quite short (α phase: about 2 minutes, β phase: about 20 minutes). But a pharmaceutical composition for use in a method comprising administration of an effective amount of PEG-modified HGF having improved pharmacokinetics in vivo and improved activities to a patient for treating hepatic diseases, treating renal diseases, promoting growth epithelial cells, treating cancer, reducing side effects of anti-cancer reagents, treating lung diseases, treating gastric and duodenal diseases, treating cerebral and nerval injury, increasing platelets, treating hypoptoteinemia, healing wounds, increasing hemopoietic stem cells, restoring hair, and in skin cosmetics, has not been reported.

The subject of the present invention is to provide a PEG-modified HGF that can maintain bioactivities in vivo for a longer time to reduce the amount of administration, and has a specificity to targeting organ.

DISCLOSURE OF THE INVENTION

As a result of extensive study, the present inventors have succeeded in obtaining a PEG-modified HGF that has improved properties in vivo and prolonged HGF activities.

The present invention provides a PEG-modified HGF.

The present invention also provides;

a PEG-modified HGF comprising HGF modified by a PEG reagent that modifies an amino group of lysine or N-terminal of a protein;

a PEG-modified HGF comprising HGF modified by a PEG reagent that modifies an amino group of lysine or N-terminal of a protein linked through an amide bond;

a PEG-modified HGF which is obtained by a process comprising the steps of, activating a carboxyl group of a PEG agent represented by the formula (1):

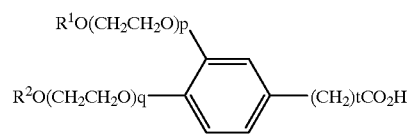

(1)

(wherein $R^1$ and $R^2$ are the same or different and independently a lower alkyl; p and q are the same or different and independently an integer selected from the range of from 20 to 280; and t is 0 or a positive integer), and treating said activated reagent with HGF; and a PEG-modified HGF which is obtained by a process comprising the steps of, activating a carboxyl group of a PEG agent represented by the formula (2):

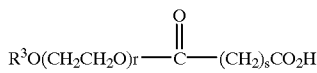

(2)

(wherein $R^3$ is a lower alkyl, r is an integer selected from the range of from 20 to 280, and s is a positive integer), and treating said activated reagent with HGF.

Present invention also provides a pharmaceutical composition for use in a method comprising administration of an effective amount of a PEG-modified HGF to a patient for treating hepatic diseases, treating renal diseases, promoting growth epithelial cells, treating cancer, reducing side effects of anti-cancer reagents, treating lung diseases, treating gastric and duodenal diseases, treating cerebral and nerval injury, increasing platelets, treating hypoptoteinemia, healing wounds, increasing hemopoietic stem cell, restoring hair, and in skin cosmetics.

The present invention also provides a method of using a PEG-modified HGF comprising the step of manufacturing a pharmaceutical composition for treating hepatic diseases, treating renal diseases, promoting growth epithelial cells, treating cancer, reducing side effects of anti-cancer reagents, treating lung diseases, treating gastric and duodenal diseases, treating cerebral and nerval injury, increasing platelets, treating hypoptoteinemia, healing wounds, increasing hemopoietic stem cells, restoring hair, and in skin cosmetics.

BEST MODE TO CARRY OUT THE PRESENT INVENTION

Figure 1:
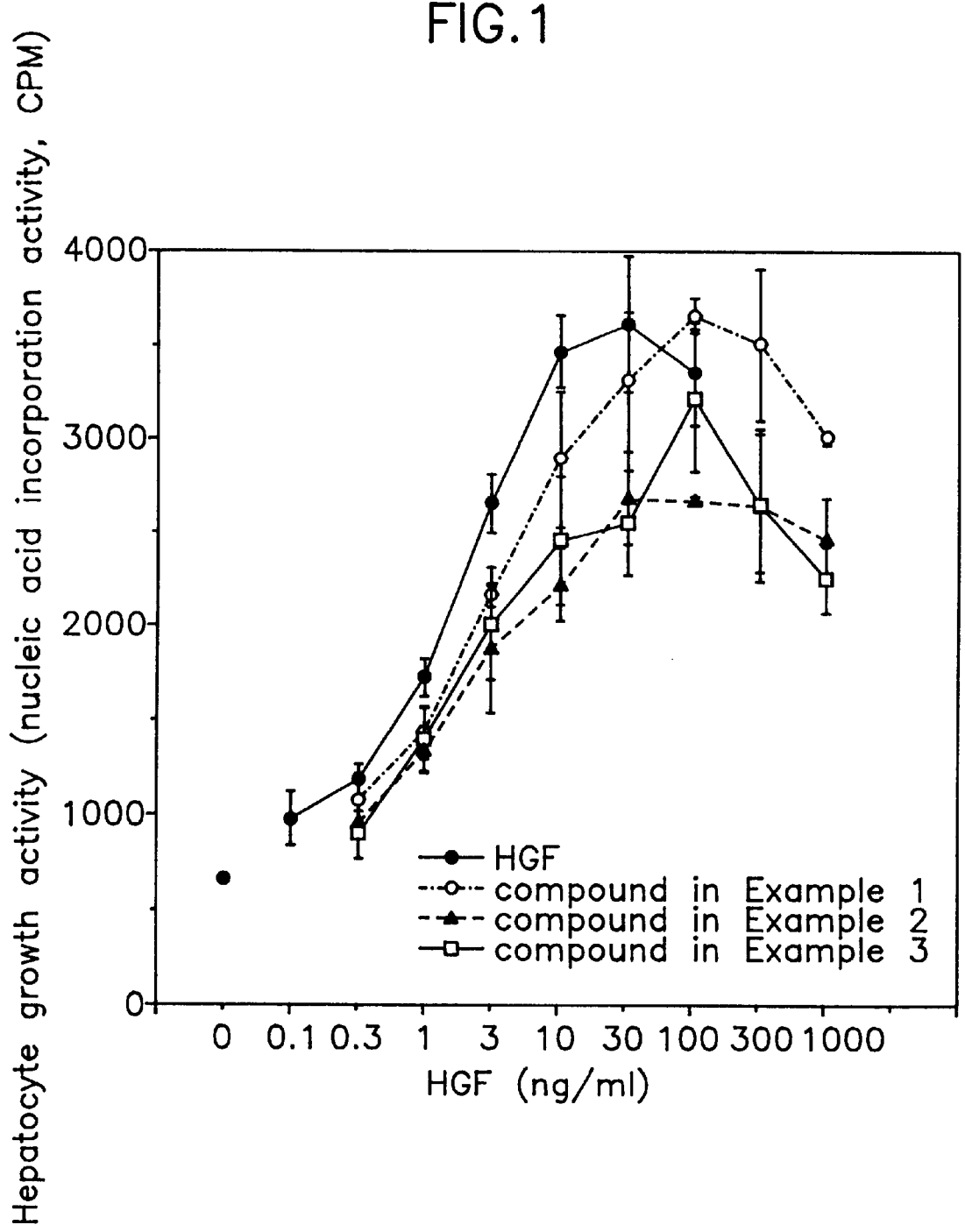
FIG. 1 shows hepatocyte growth activity of a PEG-modified HGF.

In the present invention, HGF prepared by various methods can be used.

The methods of preparing HGF are well known to a person skilled in the art. For example, HGF may be prepared by a process comprising the steps of;

extracting from an organ (such as liver, spleen, lung, bone marrow, brain, kidney, placenta and the like), blood cells (such as platelets, white blood cells and the like), plasma, serum and the like, of a mammal (such as rat, bovine, horse, sheep and the like); and purifying (FEBS Letters, 224, 312, 1987; Proc. Natl. Acad. Sci. USA, 86, 5844, 1989, etc.).

HGF may also be prepared by a process comprising the steps of;

culturing cells in primary culture or a cell line which produce(s) HGF; extracting from the culture products (supernatant fluid, cultured cells, etc.); and purifying.

HGF may also be prepared by a genetic engineering method comprising the steps of;

inserting a gene encoding HGF to an appropriate vector; transfecting a host cell by inserting said inserted vector; and purifying from the supernatant fluid of the cultured transfected cells (for example, Nature, 342, 440, 1989; Japanese patent application KOKAI 5-111383 (1993); Japanese patent application KOKAI 3-255096 (1991); Biochem. Biophys. Res. Commun., 163, 967, 1989).

Said host cell is not limited, and various host cells conventionally used in genetic engineering methods can be used, which are, for example, *Escherichia coli, Bacillus subtilis,* yeast, mold fungi, plant or animal cells and the like.

A more specific process of preparing HGF from a living tissue comprises the steps of;

administering carbon tetrachloride to a rat intraperitoneally to make said rat hepatitis; removing a liver from said rat and homogenizing; and purifying by a conventional method of protein purification such as gel column chromatography (such as S-Sepharose, heparin-sepharose and the like), HPLC and the like.

HGF may be prepared by a genetic engineering process comprising the steps of;

transforming an animal cell (such Chinese Hamster Ovary (CHO) cells, mouse C127 cells, monkey COS cells, Sf (*Spodoptera frugiperda*) cells and the like) with a gene encoding amino acid sequence of HGF; and purifying from the supernatant fluid of the cultured cells.

HGF includes human HGF and mammalian HGF, preferred HGF is a human HGF, and more preferred HGF is a human recombinant HGF (Japanese patent application KOKAI 5-111383 (1993)).

HGF prepared by the above processes includes any HGF that has substantially the same activities such as a partial deletion derivative of the amino acid sequence, a substitution derivative of an amino acid, an insertion derivative of other amino acid sequence, a derivative from binding one or more amino acids to N- or C-terminus of the amino acid sequence, or sugar chain deletion or substitution derivatives.

In the present specification, "PEG-modified" includes modifying a protein with a PEG reagent.

A PEG reagent means having a portion of a polyethylene group;

(wherein n is an integer selected from the range of from 20 to 280) and a portion to be able to bind to a protein.

There are many PEG reagents that may be used in the invention and examples of preferred PEG reagent include the three types described below.

1. A PEG reagent modifying an amino group of lysine or the N-terminus of a protein A PEG reagent modifying an amino group of lysine or the N-terminus of a protein comprises a reagent having a group that can bind to a protein, such as a carboxyl group, a derivative of carboxyl group, a carbonate ester group, formic group and the like. Examples of the PEG reagent modifying an amino group of lysine or the N-terminus of a protein are described in the reports cited below.

① Reagent modifying HGF through an amide bond

1) Tetrahedron, 40, 1581 (1961).
2) Anal. Biochem., 131, 25 (1983)
3) Cancer Biochem. Biophys., 7, 175 (1984)
4) Proc. Natl. Acad. Sci. USA, 84, 1487 (1987)
5) FEBS Letters, 223, 361 (1987)
6) Japanese patent application KOKAI 61-249388 (1986)
7) Japanese patent application KOKAI 1-316400 (1989)
8) Japanese patent application KOKAI 4-108827 (1992)

The reagents described in the reports are represented below;

$R^4O(CH_2CH_2O)_d$—$CO_2H$ $R^4O(CH_2CH_2O)_d$—$CH_2CO_2H$ $R^4O(CH_2CH_2O)_d$—$CH_2CH_2NHCO(CH_2)_iCO_2H$

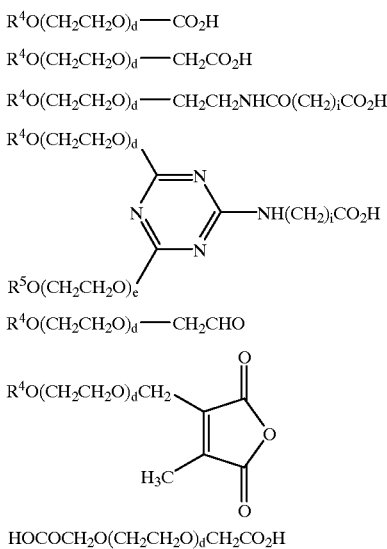

$R^4O(CH_2CH_2O)_d$—$CH_2CHO$ $HOCOCH_2O(CH_2CH_2O)_dCH_2CO_2H$ (wherein $R^4$ and $R^5$ are same or different and independently a lower alkyl, d and e are the same or different and independently an integer selected from the range of from 20 to 280, and i is a positive integer).

With these above reagents, the preferred range of i is from 1 to 10, and more the preferred range of i is from 1 to 4.

② A reagent modifying HGF through a bond other than ①

1) J. Biol. Chem., 257, 3578 (1977)
2) Chem. Lett., 773 (1980)
3) Res. Commun. Chem. Pathol. Pharmacol., 29, 113 (1980)
4) Agr. Biol. Chem., 52, 1575 (1988)
5) J. Biomatter. Sci. Polymer, Edn., 2, 61 (1991)
6) Japanese patent application KOKAI 61-178926 (1986)
7) Japanese patent application KOKAI 63-10800 (1988)

The reagents described in the reports are represented below;

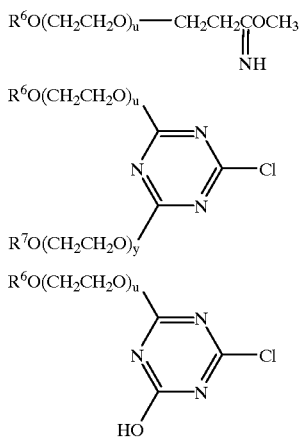

(wherein $R^6$ and $R^7$ are the same or different and independently a lower alkyl, and u and y are the same or different and independently an integer selected from the range of from 20 to 280).

2. PEG reagent modifying a carboxyl group of aspartic acid, glutamic acid or the C-terminus of a protein A PEG reagent modifying a carboxyl group of aspartic acid, glutamic acid or the C-terminus of a protein comprises a reagent having a group that can bind to a protein, such as an amino group and the like. Examples of the PEG reagent are described in Japanese patent application KOKAI 56-23587 (1981) and the like;

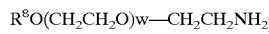

(wherein $R^8$ is a lower alkyl, and w is an integer selected from the range of from 20 to 280).

3. PEG reagent modifying a guanidino group of arginine

A PEG reagent modifying a guanidino group of arginine comprises a reagent having a group that can bind to a polypeptide or protein, such as phenylglyoxal and the like. Examples of the PEG reagent are a reagent described in Japanese patent application KOKAI 2-117920 (1990) or Japanese patent application KOKAI 3-88822 (1991);

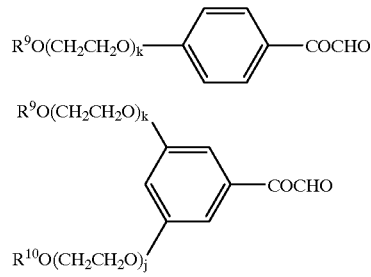

(wherein $R^9$ and $R^{10}$ are the same or different and independently a lower alkyl, and k and j are the same or different and independently an integer selected from the range of from 20 to 280).

Preferred examples of the PEG reagent are a PEG reagent modifying an amino group of lysine or the N-terminus of a protein and the like. More preferred examples of the PEG reagent are a PEG reagent modifying an amino group of lysine or the N-terminus of a protein through an amide bond.

The PEG reagent may be prepared by a conventional method well known to the skilled in the art of organic chemistry. For example, the PEG reagents may be prepared by the methods described in the above prior art.

The preparation of the PEG-modified HGF using the PEG reagent can be carried out by a conventional method well known to the skilled in the art of organic chemistry. For example, the PEG-modified HGF may be prepared by the method described in the above prior art.

A detailed method is exemplified below using a PEG reagent that has a carboxyl group in a molecule.

The PEG modification may be accomplished by the two-step reactions described below.

1. Activating a carboxyl group of the PEG reagent

Examples of methods of activating a carboxyl group are an activated ester method, a mixed anhydride method, and the like. Methods of activating a carboxyl group are described in Seikagaku Jikken Kouza Vol 1, Tanpakushitu No Kagaku IV 236–242 (Tokyo Kagaku Dojin) and Peptide Gousei No Kiso To Jikken (Izumiya et al., Maruzen).

Examples of the activated ester are p-nitrophenyl ester; thiophenyl ester; p-nitrothiophenyl ester; 1,3,5-trichlorophenyl ester; pentachlorophenyl ester; pentafluorophenyl ester; 2,4-dinitrophenyl ester; cyanomethyl ester; dicarbonicimide ester such as N-hydroxyphthalimide ester, N-hydroxysuccinimide ester and the like; activated hydroxylamine ester such as N-hydroxypeperidine ester, N-hydroxy-5-norbornene-2,3-dicarbonic acid ester and the like; and the like.

The activated ester may be prepared by a conventional organic chemistry preparation method of ester, such as treating a carboxyl group of the PEG reagent with an alcohol derivative corresponding to the activated ester in the presence of a condensing reagent such as dicyclohexylcarbodiimide, 1-ethyl-3-(3-dimethylaminopropyl) carbodiimide and the like at a temperature ranging from −20° C. to room temperature for from 1 to 24 hours.

The activated ester may also be prepared by treating a carboxyl group of the PEG reagent with a halogenated derivative corresponding to the activated ester in the presence of a base such as triethylamine and the like at a temperature ranging from 0° C. to 80° C. for from 1 to 72 hours.

The activated ester prepared by the method described above may be used in the next reaction immediately after working up, when the activated ester is unstable. The stable activated ester may be isolated and may be stored for a long time.

The mixed anhydride may be prepared by treating a carboxyl group of the PEG reagent with iso-butylchloroformate, ethylchloroformate, pivaloyl chloride, isovalerile chloride, diphenylphosphyl chloride and the like in the presence of base such as N-methylmorphorine, N-ethylpiperidine and the like at a temperature ranging from −20° C. to 0° C. for from 1 to 30 minutes. The mixed anhydride obtained in above method may be used in next reaction without isolation or purification.

2. Treating HGF with the PEG reagent having an activated carboxyl group

The reaction of a PEG reagent having an activated carboxyl group and HGF may be carried out at a temperature selected from the range such that activity of HGF can be maintained. A preferred temperature range is from 0 to 25° C.

A molar amount of the PEG reagent may be selected from the range of from 5 to 100 times of the molar of HGF. In the case of modifying an amino group of lysine or the N-terminus of protein, a preferred molar range of the PEG reagent is from 10 to 25 times of the molar of HGF.

Since the PEG reagent represented by the formulae (1) or (2) that can be used in the invention may be treated in the reaction at a pH of more than 5.5, the pH of the modifying reaction can be selected from a pH range of more than 5.5, where HGF is not deactivated. A preferred pH of the modifying reaction may be selected from the range of from 7 to 9.

A reaction solvent may be selected from solvents that are inert to the reaction. Examples of the reaction solvent are a buffer solution such as phosphate buffer solution, tris buffer solution, borate buffer solution, aqueous sodium carbonate solution, aqueous sodium hydrogencarbonate solution, N-ethylmorpholine-acetic acid buffer solution, sodium maleate buffer solution, sodium acetate buffer solution and the like.

An organic solvent that does not deactivate HGF and is inert to the reaction may be added to the solvent, and examples of such organic solvent are a lower alcohol such as methanol, ethanol, propanol and the like; acetonitrile; dioxane; tetrahydrofuran; and the like.

The reaction time is selected from the range of from 1 to 72 hours.

After the termination of the reaction, the PEG-modified HGF may be purified from the reaction mixture by a conventional purification method of a protein, such as salting-out, gel filtration, ion-exchange chromatography, adsorptive chromatography, affinity chromatography, ultrafiltration, reverse phase HPLC and the like.

The lower alkyl as used in $R^1$–$R^{10}$ of the PEG reagent in the invention includes a straight and branched alkyl having 1 to 6 carbon atoms. Examples of lower alkyl are methyl, ethyl, propyl, iso-propyl, butyl, pentyl, hexyl and the like.

The PEG-modified HGF of the present invention may be formulated in various ways such as liquid preparations, solid preparations, capsule preparations and the like. The PEG-modified HGF of the present invention may be formulated for parenteral administration for injection without any carrier or with an appropriate conventional carrier and for oral administration with an appropriate conventional carrier. The preparation for parenteral administration for injection may be prepared by a conventional method, such as a method comprising the steps of;

dissolving the PEG-modified HGF in an appropriate solvent such as sterilized water, buffered solution, physiological saline solution and the like;

sterilizing by filtration; and filling a sterilized bottle with said solution.

An amount of the PEG-modified HGF in the parenteral preparation is from about 0.0002 to about 0.2 (W/V%), and preferably from about 0.001 to about 0.1 (W/V%). The preparation may be prepared by the conventional preparation technique. The amount of the PEG-modified HGF may be varied depending on preparation form, disease to be treated and the like.

A stabilizer may be added to the preparation, and examples of the stabilizer are albumin, globulin, gelatin, mannitol, glucose, dextran, ethylene glycol and the like. The preparation of the present invention may include a necessary additive such as an excipient, a solubilizing agent, an antioxidant agent, a pain-alleviating agent, an isotonic agent and the like. In the liquid preparation, it is preferable to store it under frozen condition or after removal of water by a process such as freeze-drying. The freeze-dried preparation is used by dissolving again in distilled water for injection and the like before use.

An administration route of the preparation of the present invention may vary depending on the form of preparation. The parenteral preparation may be administered intravenously, intraarterially, subcutaneously or intramuscularly. The amount of dose may vary depending on symptom, age, body weight, etc of a patient. The dose of PEG-modified HGF is calculated as the HGF portion of PEG-modified HGF and is selected from the range of from 0.1 μg/kg to 10 mg/kg. The preparation of PEG-modified HGF may be administered once or several times per day.

The utility of the present invention

The PEG-modified HGF of the present invention is considered to act on cells in the same mechanism as HGF, through the protein portion of the PEG-modified HGF. The PEG-modified HGF has same biological activities as HGF.

The HGF modified by the PEG reagent represented by the formulae (1) and (2) has an improved pharmacokinetic activity in vivo, and more specificity to an organ compared to the non-modified HGF and shows same activities in lower dose.

The PEG-modified HGF has a prolonged clearance in vivo and shows retained biological activities. The PEG-modified HGF has the same activities as non-modified HGF. Therefore the PEG-modified HGF is useful as a pharmaceutical composition for treating hepatic diseases, treating renal diseases, promoting growth of epithelial cells, treating cancer, reducing side effects of anti-cancer reagents, treating lung diseases, treating gastric and duodenal diseases, treating cerebral and nerval injury, increasing platelets, treating hypoptoteinemia, healing wounds, increasing hemopoietic stem cell, restoring hair, and in skin cosmetics.

EXAMPLES

The following examples are for illustrative purposes only and are not to be construed as limiting the invention.

The data of amino acid analysis in the examples are the results in the acid decomposition of the modified HGF (decomposition products after treating with 6 N hydrochloric acid-phenol at 110° C. for 24 hours).

The rate of modified amino group is calculated from the method of trinitrobenzene sulfonic acid (Methods in Enzymology, vol.25, p464 (1972). Academic Press, New York) comparing to non-modified HGF.

Each abbreviation means the following respectively.

Asx: Aspartic acid or Asparagine
Glx: Glutamic acid or Glutamine
Ser: Serine
Gly: Glycine
His: Histidine
Arg: Arginine
Thr: Threonine
Ala: Alanine
Pro: Proline
Tyr: Tyrosine
Val: Valine
Met: Methionine
Ile: Isoleucine
Leu: Leucine
Phe: Phenylalanine
Lys: Lysine

Example 1

HGF modified by 3,4-bis-methoxypolyethyleneglycolhydrocinnamic acid

To a 30 mM phosphate buffer solution (pH 6.0, 0.3 M-NaCl) (6.9 ml) was added HGF (3.90 mg) and the pH was adjusted to 8.25 with 1 N NaOH solution. To the solution was added 3,4-bis-methoxypolyethyleneglycolhydrocinnamic acid N-hydroxysuccinimide ester (average molecular weight is about 10,000) (3.14 mg, 0.15 equivalent to the amino groups) and the reaction mixture was stirred for 18 hours at room temperature. The pH of the reaction mixture was adjusted to 6.5 with 0.1 N HCl and the reaction mixture was purified by gel filtration chromatography (Column: Sephacryl S-200HR 2.6 cmø×90 cm, Eluent: 0.2 M aqueous NaCl solution, Flow rate: 1.4 ml/min., Detection wave length: 220 nm). The objective fractions were collected and subjected to desalting and concentrating by ultrafiltration with YM-15 membrane (Amicon) to give an aqueous solution (750 ml) of titled compound (content of protein: 3.713 mg/ml, modifying rate of amino acid; 19%).

Amino acid analysis

Asx 63.2 (83), Glx 50.5 (59), Ser 30.1 (38), Gly 54.0 (57), His 20.2 (22), Arg 33.3 (41), Thr 31.9 (38), Ala* 21.0 (21), Pro 35.0 (44), Tyr 24.4 (32), Val 26.5 (33), Met 11.4 (15), Ile 32.1 ( 37), Leu 35.5 (37), Phe 16.0 (17), Lys 41.4 (41), Cys - (40)

*: standard amino acid, ( ): calculated data, -: data not measured

GPC

Column: TSK gel G3000SW 7.5 mmø×600 mm (manufactured by Toso Co., Ltd.)
Eluent: 10 mM Tris buffer, 0.2 M aqueous NaCl solution, 0.05% SDS
Flow rate: 0.6 ml/min.
Detection wave length: 220 nm
Retention time: 18.517 min.

Example 2

HGF modified by 3,4-bis-methoxypolyethyleneglycolhydrocinnamic acid

To a 30 mM phosphate buffer solution (pH 6.0, 0.3 M-NaCl) (6.9 ml) was added HGF (3.90 mg) and the pH was adjusted to 8.25 with 1N NaOH solution. To the solution was added 3,4-bis-methoxypolyethyleneglycolhydrocinnamic acid N-hydroxysuccinimide ester (average molecular weight is about 10,000) (6.29 mg, 0.3 equivalents to the amino groups) and the reaction mixture was stirred for 18 hours at room temperature. The pH of the reaction mixture was adjusted to 6.5 with 0.1 N HCl and the reaction mixture was purified by gel filtration chromatography (Column: Sephacryl S-200HR 2.6 cmø×90 cm, Eluent: 0.2 M aqueous NaCl solution, Flow rate: 1.4 ml/min., Detection wave length: 220 nm). The objective fractions were collected and subjected to desalting and concentrating by ultrafiltration with YM-15 membrane (Amicon) to give an aqueous solution (1.00 ml) of titled compound (content of protein: 3.722 mg/ml, modifying rate of the amino groups; 32%).

Amino acid analysis

Asx 64.4 (83), Glx 52.2 (59), Ser 30.6 (38), Gly 54.8 (57), His 20.2 (22), Arg 33.7 (41), Thr 32.5 (38), Ala* 21.0 (21), Pro 35.4 (44), Tyr 25.2 (32), Val 26.8 (33), Met 12.5 (15), Ile 32.8 ( 37), Leu 35.7 (37), Phe 16.2 (17), Lys 41.9 (41), Cys - (40)

*: standard amino acid, ( ): calculated data, -: data not measured

GPC

Column: TSK gel G3000SW 7.5 mmø×600 mm (manufacture by Toso Co., Ltd.)
Eluent: 10 mM Tris buffer, 0.2 M aqueous NaCl solution, 0.05% SDS
Flow rate: 0.6 ml/min.
Detection wave length: 220 nm
Retention time: 18.183 min.

Example 3

HGF modified by monomethoxypolyethylenglycolsuccinic acid

To a 30 mM phosphate buffer solution (pH 6.0, 0.3 M-NaCl) (6.85 ml) was added HGF (3.87 mg) and the pH was adjusted to 8.24 with 1N NaOH solution. To the solution was added monomethoxypolyethyleneglycolsuccinic acid N-hydroxysuccinimide ester (average molecular weight is about 5,000) (3.14 mg, 0.3 equivalents to the amino groups) and the reaction mixture was stirred for one hour at room temperature. The pH of the reaction mixture was adjusted to 6.5 with 0.1 N HCl and the reaction mixture was purified by gel filtration chromatography (Column: Sephacryl S-200HR 2.6 cmø×90 cm, Eluent: 0.2 M aqueous NaCl solution, Flow rate: 1.4 ml/min., Detection wave length: 220 nm). The objective fractions were collected and subjected to desalting and concentrating by ultrafiltration with YM-15 membrane (Amicon) to give an aqueous solution (1.60 ml) of titled compound (content of protein: 1.813 mg/ml, modifying rate of the amino groups; 33%).

Amino acid analysis

Asx 62.5 (83), Glx 49.8 (59), Ser 31.0 (38), Gly 55.1 (57), His 19.4 (22), Arg 33.3 (41), Thr 31.8 (38), Ala* 21.0 (21), Pro 35.5 (44), Tyr 23.9 (32), Val 26.9 (33), Met 13.0 (15), Ile 31.9 (37), Leu 35.8 (37), Phe 16.1 (17), Lys 40.9 (41), Cys - (40)

*: standard amino acid, ( ): calculated data, -: data not measured

GPC

Column: TSK gel G3000SW 7.5 mmø×600 mm (manufacture by Toso Co., Ltd.)

Eluent: 10 mM Tris buffer, 0.2 M aqueous NaCl solution, 0.05% SDS

Flow rate: 0.6 ml/min.

Detection wave length: 220 nm

Retention time: 18.225 min.

Example 4

The activities in vitro of PEG-modified HGF's obtained in Examples 1, 2, and 3 were measured with hepatocyte primary cultures. The hepatocytes were obtained from Wister rats (Male, 8 to 10-week old) and were cultured.

The rat hepatocytes were isolated and cultured according to the method by Nakamura (Shodai-baiyou-kansaibou-jikken-hou, Gakkai-shuppan Center (1989)). Isolated hepatocytes were cultured for 24 hours in a medium comprising William's E (WE) medium containing 5% FCS, and were cultured in the serum-free medium containing various concentrations of the sample for 20 hours, in wells.

About 2 kBq/well of 5-[$^{125}$I]-iododeoxyuridine ($^{125}$I-Urd) was added to each well, and the cells were cultured for further 4.5 hours to incorporate $^{125}$I-Urd into the cells. After the cultivation, the plate was washed with PBS (-), and was fixed with 10% TCA. The cells were dissolved in 1 N NaOH and the amount of RI incorporated into the cells was measured using a γ-counter. The results are shown in FIG. 1.

The relative activity at 1 ng/ml and 3 ng/ml was calculated with a two x two point method. The relative activity of the compound of Example 1 is 0.60, the relative activity of the compound of Example 2 is 0.42 and the relative activity of the compound of Example 3 is 0.50.

Example 5

Pharmocokinetics of the compound of Example 1 and 2 was studied. Wister rat (male, 11-week old) purchased from Nihon SLC was used.

1) Labeling HGF and the PEG-modified HGF

Each compound was labeled by the Iodogen method. The labeling was confirmed by way of treating the labeled compound with 10% trichloroacetic acid immediately after the labeling. As a result, more than 96% of isotope was recovered in the precipitate fraction. The labeled compound was frozen and stored at −80° C.

2) Preparation of labeled compound for measurement of pharmacokinetics

A cold sample corresponding to the labeled compound was dissolved in PBS solution containing 2.5 mg/ml HAS and 0.01% Tween 80 to give a cold sample concentration of 0.25 mg/ml. A sample for pharmacokinetic test was prepared by adding the labeled compound obtained from trichloroacetic acid precipitate fraction ($2.2 \times 10^7$ cpm) to the cold sample. The protein amount of labeled compound added to the sample for pharmacokinetic test was less than 4% of the cold sample. Final concentration of HGF in the sample for pharamacokinetics test was 0.23 mg/ml.

3) Administration to rats and preparation of blood sample

Each sample was administered to rats via a tail vein and an amount of administration was 2 ml/kg. The rats were divided to two groups (n=2). After the administration, blood samples was collected from the orbital venous plexus at 2, 5, 10 and 30 minutes from one group and at 10, 20, 30, 45 and 60 from the other group.

4) Separation of serum and measurement of an isotope amount

The collected blood samples were separated to give serum. The serum (100 μl) was put into a tube, 10% trichloroacetic acid was added and centrifuged, and the supernatant was removed to give a precipitate fraction. The amount of isotope in the precipitate was presumed to arise the labeled HGF and PEG-modified HGF, and measured by the γ-counter. From the results, the time-dependent concentration curves were calculated and are shown in FIG. 2.

From the time-dependent curve, an initial concentration of the sample was derived and the amount of administration was confirmed.

Figure 2:
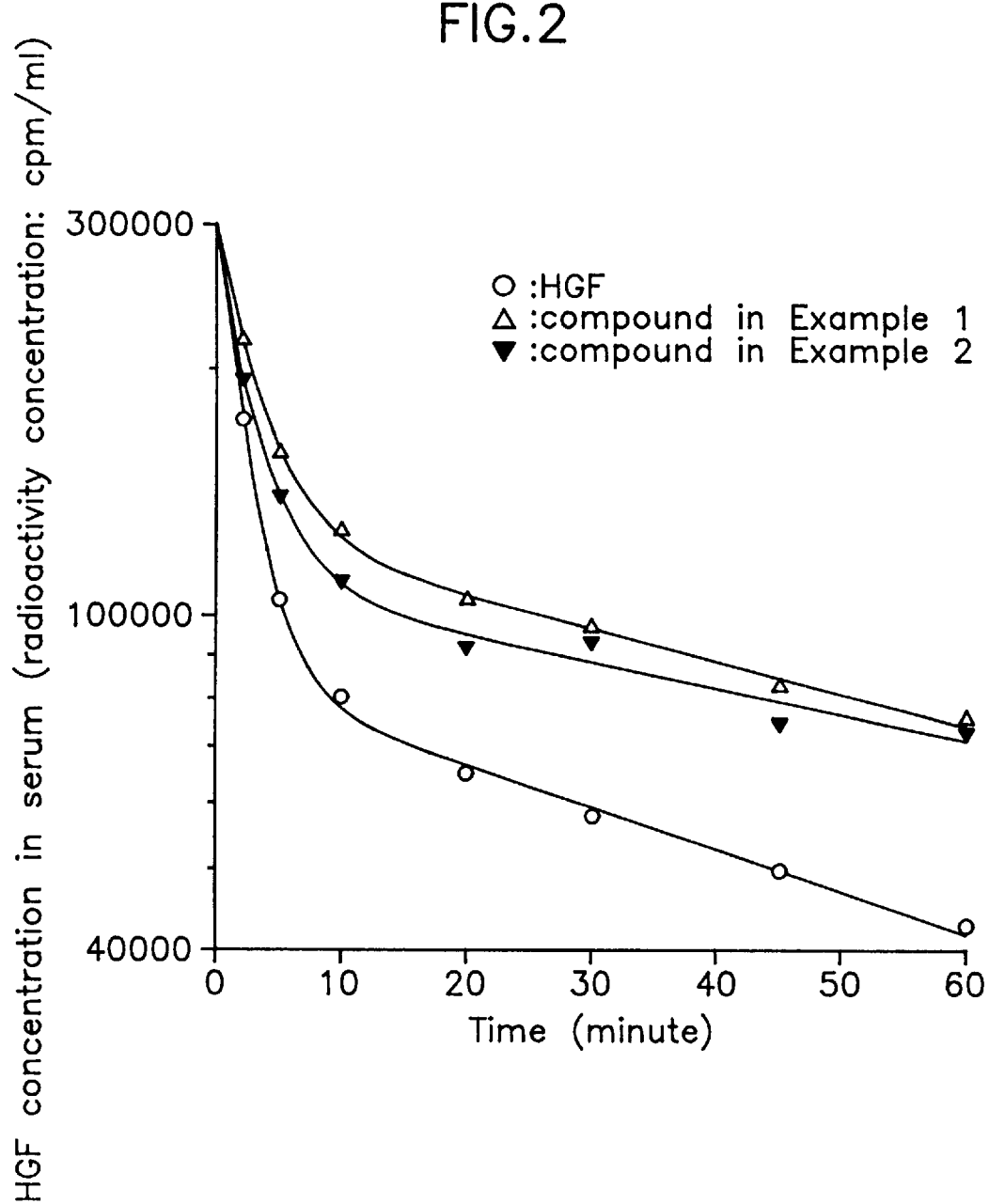
FIG. 2 shows time dependent concentration of a PEG-modified HGF in blood.

The half life time of the each sample was calculated from FIG. 2. The half life time of HGF was 59.2 minutes and the half life times of the compound in Example 1 and 2 were 76.7 and 95.6 minutes, respectively. It was revealed that the PEG-modified HGF has a improved stability in vivo and prolonged activities.

Example 6

HGF modified by 3,4-bis-methoxypolyethyleneglycolhydrocinnamic acid

To a 10 mM phosphate buffer solution (pH 6.5, 1 M-NaCl, 0.01% Tween 80) (3.19 ml) was added HGF (148.3 mg) and 0.1 M borate buffer solution (11.64 ml, pH8.21, 1 M-NaCl) and the pH was adjusted to 8.21 with 1 N NaOH solution. To the solution was added 3,4-bis-methoxypolyethyleneglycolhydrocinnamic acid N-hydroxysuccinimide ester (average molecular weight is about 10,000) (239.2 mg, 0.3 equivalents to the amino groups) and the reaction mixture was stirred for 18 hours at room temperature. The pH of the reaction mixture was adjusted to 6.5 with 0.1 N HCl, and the reaction mixture was divided to 6 portions and each portion was purified by gel filtration chromatography (Column: Sephacryl S-200HR 2.6 cmø×90 cm, Eluent: 0.2 M aqueous NaCl solution, Flow rate: 1.4 ml/min., Detection wave length: 220 nm). The objective fractions were collected and subjected to concentrating by ultrafiltration with YM-15 membrane (Amicon) to give an 0.15 M NaCl aqueous solution (21.0 ml) of titled compound (content of protein: 4.73 mg/ml, modifying rate of the amino groups; 29%).

Amino acid analysis

Asx 70.3 (83), Glx 55.9 (59), Ser 34.0 (38), Gly 56.0 (57), His 23.1 (22), Arg 40.7 (41), Thr 32.1 (38), Ala* 21.0 (21),

Pro 38.2 (44), Tyr 27.7 (32), Val 26.8 (33), Met 18.1 (15), Ile 32.5 ( 37), Leu 33.9 (37), Phe 15.4 (17), Lys 42.5 (41), Cys - (40)

*: standard amino acid, ( ): calculated data, -: data not measured

GPC

Column: TSK gel G3000SW 7.5 mmø×600 mm (manufacture by Toso Co., Ltd.)

Eluent: 10 mM Tris buffer, 0.2 M aqueous NaCl solution, 0.05% SDS

Flow rate: 0.6 ml/min.

Detection wave length: 220 nm

Retention time: 17.95 min.

Example 7

To compare pharmaceutical activities of HGF and the PEG-modified HGF in Example 6, HGF and the PEG-modified HGF which have the same protein amount calculated as HGF were administered to rats and an enhancing activity on production of fibrinogen in liver was measured.

HGF and the PEG-modified HGF were dissolved in 10 mM citric acid buffer solution (pH 5) containing 0.3 M NaCl and 0.01% Tween 80, respectively. Administration doses of HGF and the PEG-modified HGF were 0.05, 0.15 and 0.5 mg of HGF protein/kg body weight. The sample was administered to rats via tail vein two times a day. One group consists of five rats. Next day of the two-day administration, rats were anesthetized and a blood sample was collected from abdominal vein. The sample was treated with citric acid and an amount of fibrinogen (mg/dl) was measured using automatic device for measuring blood coagulation (CA 5000, Cysmex).

Figure 3:
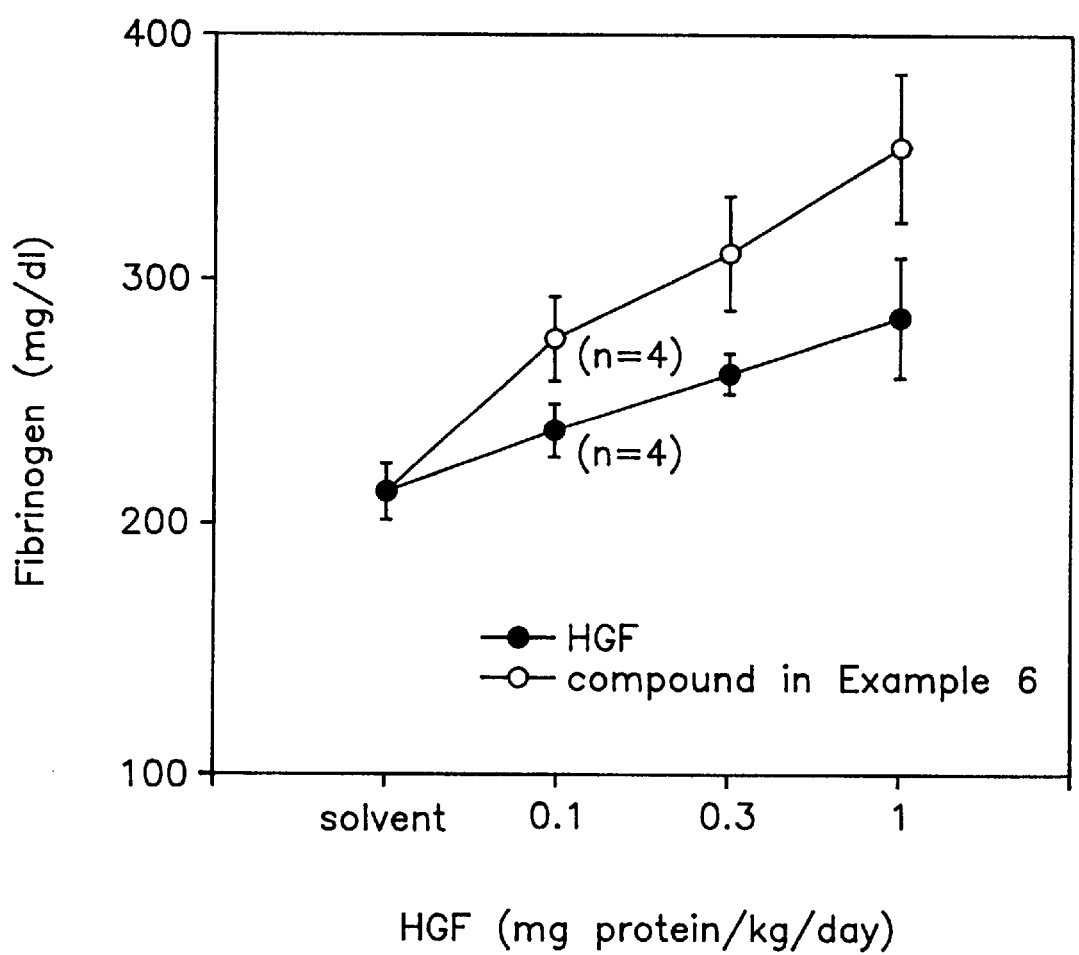
FIG. 3 shows an enhancing activity of a PEG-modified HGF on production of protein (fibrinogen).

The results are shown in FIG. 3.

The activity of the samples was compared by the method of 2×2 parallel test at 0.3 mg/kg/day and 1 mg/kg/day. The PEG-modified HGF showed 8.6 times activity of HGF.

We claim:

1. HGF modified by a PEG reagent obtained by a process comprising the following steps:

activating a carboxyl group of a PEG reagent represented by the formula (1):

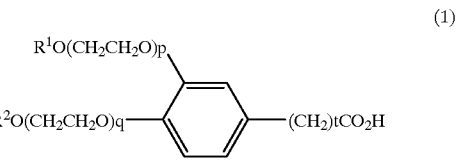
(1)

wherein $R^1$ and $R^2$ are the same or different and independently a lower alkyl; p and q are the same or different and independently an integer from 20 to 280; and t is 0 or a positive integer; and reacting HGF with said activated PEG reagent.

2. The HGF modified by a PEG reagent of claim 1, wherein the lower alkyl is a straight or branched alkyl having 1 to 6 carbon atoms.

* * * * *